United States Patent
Stoiljkovic et al.

(10) Patent No.: US 11,939,712 B2
(45) Date of Patent: Mar. 26, 2024

(54) MELTBLOWN NONWOVEN FABRICS, AND COMPOSITES THEREOF

(71) Applicant: Dow Global Technologies LLC, Midland, MI (US)

(72) Inventors: Aleksandar Stoiljkovic, Waedenswil (CH); Eduardo Alvarez, Tarragona (ES); Yijian Lin, Pearland, TX (US)

(73) Assignee: Dow Global Technologies, LLC, Midland, MI (US)

( * ) Notice: Subject to any disclaimer, the term of this patent is extended or adjusted under 35 U.S.C. 154(b) by 0 days.

(21) Appl. No.: 17/595,479

(22) PCT Filed: Jul. 20, 2020

(86) PCT No.: PCT/US2020/042763
§ 371 (c)(1),
(2) Date: Nov. 17, 2021

(87) PCT Pub. No.: WO2021/021480
PCT Pub. Date: Feb. 4, 2021

(65) Prior Publication Data
US 2022/0251748 A1    Aug. 11, 2022

Related U.S. Application Data

(60) Provisional application No. 62/879,147, filed on Jul. 26, 2019.

(51) Int. Cl.
*D04H 3/018* (2012.01)
*A61F 13/15* (2006.01)
*D04H 1/4291* (2012.01)
(Continued)

(52) U.S. Cl.
CPC ....... *D04H 3/018* (2013.01); *A61F 13/15577* (2013.01); *D04H 1/4291* (2013.01);
(Continued)

(58) Field of Classification Search
CPC .... D04H 1/724; D04H 1/4291; D04H 1/4391; D04H 3/018; D04H 3/16; D04H 3/03; A61F 13/15
See application file for complete search history.

(56) References Cited

U.S. PATENT DOCUMENTS

| 5,498,463 A | 3/1996 | McDowall et al. |
| 6,797,655 B2 | 9/2004 | Rudisill |

(Continued)

FOREIGN PATENT DOCUMENTS

| EP | 0868554 B1 | 11/2000 |
| WO | 200210497 A1 | 2/2002 |

(Continued)

OTHER PUBLICATIONS

Pu et al., "Preparation of polypropylene micro and nanofibers by electrostatic-assisted melt blown and their application," Polymers 2018, 10, 959. (Year: 2018).*

(Continued)

*Primary Examiner* — Jeremy R Pierce
(74) *Attorney, Agent, or Firm* — Boyle Fredrickson S.C.

(57) ABSTRACT

A meltblown nonwoven formed from a bicomponent fiber, wherein: the bicomponent fiber has a first region and a second region, the first region is formed from a first composition comprising at least 75 wt. % of a polypropylene; the second region is formed from a second composition comprising at least 75 wt. % of an ethylene/alpha-olefin interpolymer.

13 Claims, 2 Drawing Sheets

(51) Int. Cl.
  *D04H 1/4391* (2012.01)
  *D04H 1/724* (2012.01)
  *D04H 3/03* (2012.01)
  *D04H 3/16* (2006.01)

(52) U.S. Cl.
  CPC ........... *D04H 1/4391* (2013.01); *D04H 1/724* (2013.01); *D04H 3/03* (2013.01); *D04H 3/16* (2013.01); *A61F 2013/15552* (2013.01); *A61F 2013/15959* (2013.01); *A61F 2013/15967* (2013.01); *D10B 2509/02* (2013.01)

(56) References Cited

U.S. PATENT DOCUMENTS

| | | | |
|---|---|---|---|
| 7,049,254 B2 | 5/2006 | Bansal et al. | |
| 11,261,544 B2* | 3/2022 | Shah | D04H 1/4291 |
| 2006/0141886 A1 | 6/2006 | Brock et al. | |
| 2010/0113706 A1* | 5/2010 | Crowther | C08F 210/16 526/170 |
| 2011/0003524 A1 | 1/2011 | Claasen et al. | |
| 2014/0248816 A1* | 9/2014 | Bonavoglia | D04H 3/16 442/361 |
| 2015/0238374 A1* | 8/2015 | Wildeman | A61F 13/627 604/391 |
| 2017/0258650 A1* | 9/2017 | Rosati | D04H 1/42 |

FOREIGN PATENT DOCUMENTS

| | | |
|---|---|---|
| WO | 2002029145 A2 | 4/2002 |
| WO | 2013052638 A1 | 4/2013 |
| WO | 2017091669 A1 | 6/2017 |
| WO | 2018169738 A1 | 9/2018 |

OTHER PUBLICATIONS

Zhang, Textile Research Journal, 2001, vol. 71, No. 4, p. 301-308.
PCT/US2020/042763, International Search Report and Written Opinion dated Oct. 29, 2020.

* cited by examiner

MELTBLOWN NONWOVEN FABRICS, AND COMPOSITES THEREOF

TECHNICAL FIELD

Embodiments of the present disclosure generally relate to meltblown nonwovens formed from bicomponent fibers, and composite structures thereof.

BACKGROUND

Nonwoven fabrics (NW) are cloth-like materials that are manufactured from filaments which are brought together via different bonding techniques (e.g., spunbond or meltblown processes). These nonwoven fabrics may be used in hygiene and/or medical applications, such as, disposable absorbent articles, including diapers, wipes, feminine hygiene products, and adult incontinence products. In such applications, a spunbond meltblown spunbond (SMS) composite structure is becoming increasingly popular.

The spunbond layer was historically formed from polypropylene monocomponent fibers due to its mechanical performance One of the major drawbacks of polypropylene is the lack of softness. The softness can be addressed by the introduction of polyethylene (PE). Spunbond layers are increasingly being formed from bicomponent fibers having a polyethylene resin in the sheath and a polypropylene resin in the core. The polyethylene resin provides softness & improved haptics, a desirable feature in hygiene and/or medical applications, and the polypropylene provides strength and fiber spinnability.

Polypropylene resins are also typically used to form the meltblown layer because of its excellent processing characteristics in meltblown processes. However, in an SMS structure, the outer polyethylene sheath of the bicomponent fibers used to form the spunbond nonwoven is now bonded to a polypropylene meltblown layer. The melting temperature difference and incompatibility between polyethylene and polypropylene can create poor bonding between the layers since when the higher polypropylene melting temperature is used, the polyethylene can tend to 'run away' from the bonding point, and at the lower polyethylene melting temperature, the polypropylene does not melt properly. Thus, poor bonding strength in the SMS composite structure can result.

Accordingly, alternative resins may be desirable for use in meltblown nonwovens and in SMS composite structures that may exhibit improved bonding strength.

SUMMARY

Disclosed herein are meltblown nonwovens. The meltblown nonwovens are formed from a bicomponent fiber, wherein the bicomponent fiber has a first region and a second region. The first region is formed from a first composition comprising at least 75 wt. % of a polypropylene, and the second region is formed from a second composition comprising at least 75 wt. % of an ethylene/alpha-olefin interpolymer having a density of from 0.911 to 0.950 g/cc, a Brookfield viscosity of less than or equal to 50,000 cP, and a molecular weight distribution (Mw,cc/Mn,cc) of 1.8 to 3.5; and wherein the bicomponent fiber has a shear viscosity ratio of the first composition to the second composition of less than 2.0.

Further disclosed herein are composite structures. The composite structures comprise a meltblown nonwoven. The meltblown nonwoven is formed from a bicomponent fiber, wherein the bicomponent fiber has a first region and a second region. The first region is formed from a first composition comprising at least 75 wt. % of a polypropylene, and the second region is formed from a second composition comprising at least 75 wt. % of an ethylene/alpha-olefin interpolymer having a density of from 0.911 to 0.950 g/cc, a Brookfield viscosity of less than or equal to 50,000 cP, and a molecular weight distribution (Mw,cc/Mn,cc) of 1.8 to 3.5; and wherein the bicomponent fiber has a shear viscosity ratio of the first composition to the second composition of less than 2.0.

In one or more embodiments herein, the ethylene/alpha-olefin interpolymer has an $M_{z,cc}/M_{n,cc}$ of less than 4.0. In one or more embodiments herein, the ethylene/alpha-olefin interpolymer has a weight fraction (w) of molecular weight greater than $10^5$ g/mole, based on the total weight of interpolymer, as determined by conventional gel permeation chromatography, of less than 2.5%. In one or more embodiments herein, the ethylene/alpha-olefin interpolymer has a comonomer distribution breadth index of greater than 50%, or alternatively, from 50% to 98%, or alternatively, 50% to 85%.

In one or more embodiments herein, the bicomponent fiber has a sheath/core structure. In one or more embodiments herein, the first region of the bicomponent fiber is the core, and the second region of the bicomponent fiber is the sheath. In one or more embodiments herein, the meltblown nonwoven exhibits an air permeability of less than 500 l/m²/s at 20 gsm.

In one or more embodiments herein, the composite structure further comprises one or more spunbond nonwovens. In one or more embodiments herein, the composite structure has an SaMbSc configuration, wherein S is a spunbond nonwoven, M is a meltblown nonwoven as described herein, and a, b, and c are the number of layers and are independent integers ranging from 1 to 5. In one or more embodiments herein, the spunbond nonwoven is formed from bicomponent fibers having a sheath/core structure, wherein the sheath comprises polyethylene and the core comprises polypropylene. In one or more embodiments herein, the spunbond nonwoven is formed from monocomponent fibers, wherein the monocomponent fibers comprise polyethylene.

Additional features and advantages of the embodiments will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing and the following description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
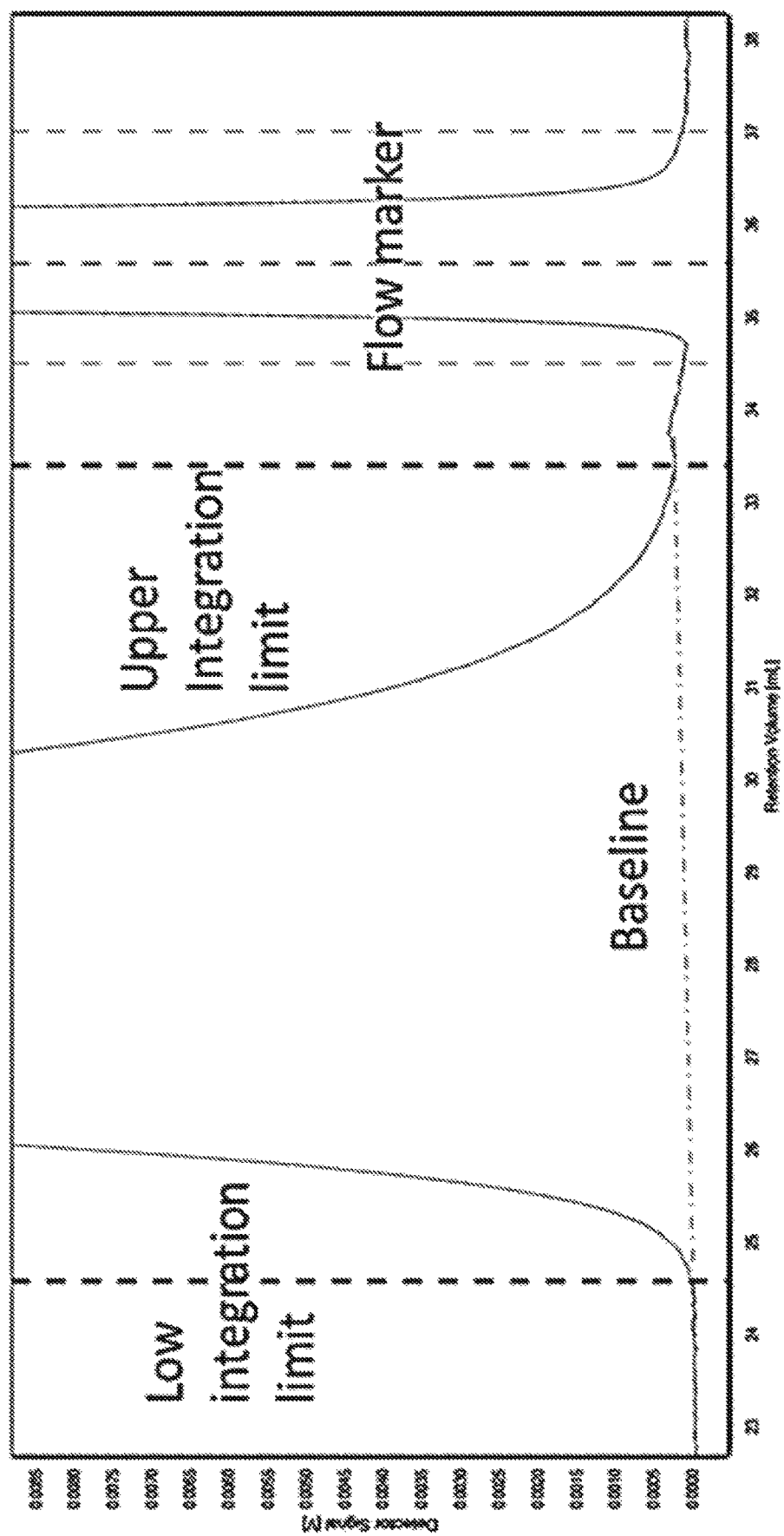
FIG. 1 graphically depicts a chromatogram plot of the detector signal (V) versus retention volume (ml) and the proper baseline and integration limit sets for a sample that exhibits a clear separate antioxidant peak.

Reference will now be made in detail to embodiments of the melt blown nonwovens. The meltblown nonwoven fabrics may be used in hygiene absorbent articles, such as, diapers, wipes, feminine hygiene, and adult incontinence products. It is noted, however, that this is merely an illustrative implementation of the embodiments disclosed herein. The embodiments are applicable to other technologies that are susceptible to similar problems as those discussed above. For example, the meltblown nonwovens may be used to produce face masks, surgical gowns, isolation gowns, surgical drapes and covers, surgical caps, tissues, bandages, and wound dressings are clearly within the purview of the present embodiments.

The meltblown nonwovens are formed from one or more bicomponent fibers having a first region and a second region. The first region is formed from a first composition comprising at least 75 wt. % of a polypropylene. All individual values and subranges of at least 75 wt. % of a polypropylene are included and disclosed herein. For example, in some embodiments, the first composition comprises at least 80 wt. %, at least 85 wt. %, at least 90 wt. %, at least 92 wt. %, at least 95 wt. %, at least 97 wt. %, at least 99 wt. %, or 100 wt. % of a polypropylene. As used herein, "polypropylene" shall mean polymers comprising greater than 50% by weight of units which have been derived from a propylene monomer. This includes homopolymer polypropylene, random copolymer polypropylene, impact copolymer polypropylene, and propylene-based plastomers and elastomers. These polypropylene materials are generally known in the art.

The first composition may also comprise up to 25 wt. % of additional components, such as, one or more other polymers and/or one or more additives. Such additives include, but are not limited to, antistatic agents, color enhancers, dyes, lubricants, fillers, pigments, primary antioxidants, secondary antioxidants, processing aids, UV stabilizers, anti-blocks, slip agents, tackifiers, fire retardants, anti-microbial agents, odor reducer agents, anti-fungal agents, and combinations thereof. In some embodiments, the first composition may comprise up to 25 wt. % of propylene based plastomers or propylene based elastomers (such as Versify and Vistamaxx), low modulus or/and low molecular weight polypropylene (such as L-Modu from Idemitsu), random copolypropylene, or propylene based olefin block copolymers (such as Intune).

The second region is formed from a second composition comprising at least 75 wt. % of an ethylene/alpha-olefin interpolymer. All individual values and subranges of at least 75 wt. % of an ethylene/alpha-olefin interpolymer are included and disclosed herein. For example, in some embodiments, the second composition comprises at least 80 wt. %, at least 85 wt. %, at least 90 wt. %, at least 92 wt. %, at least 95 wt. %, at least 97 wt. %, at least 99 wt. %, or 100 wt. % of an ethylene/alpha-olefin interpolymer.

The second composition may also comprise up to 25 wt. % of additional components, such as, one or more other polymers and/or one or more additives. Such additives include, but are not limited to, antistatic agents, color enhancers, dyes, lubricants, fillers, pigments, primary antioxidants, secondary antioxidants, processing aids, UV stabilizers, anti-blocks, slip agents, tackifiers, fire retardants, anti-microbial agents, odor reducer agents, anti-fungal agents, and combinations thereof. In some embodiments, the second composition may comprise up to 25 wt. % of ethylene based elastomers (such as Engage or Affinity), olefin block copolymers (such as Infuse), propylene based olefin block copolymers (such as Intune), liner low density polyethylenes with densities between 0.9 to 0.970 g/cc.

Ethylene/Alpha-Olefin Interpolymer

"Interpolymer" refers to a polymer prepared by the polymerization of at least two different types of monomers. The generic term "interpolymer" includes the term "copolymer" (which is usually employed to refer to a polymer prepared from two different monomers) as well as the term "terpolymer" (which is usually employed to refer to a polymer prepared from three different types of monomers). It also encompasses polymers made by polymerizing four or more types of monomers.

Ethylene/alpha-olefin interpolymer generally refers to polymers comprising ethylene and an alpha-olefin having 3 or more carbon atoms. In embodiments herein, the ethylene/alpha-olefin interpolymer comprises greater than 50 wt. % of the units derived from ethylene and less than 30 wt. % of the units derived from one or more alpha-olefin comonomers (based on the total amount of polymerizable monomers). All individual values and subranges of greater than 50 wt. % of the units derived from ethylene and less than 30 wt. % of the units derived from one or more alpha-olefin comonomers are included and disclosed herein. For example, in some embodiments, the ethylene/alpha-olefin interpolymer comprises (a) greater than or equal to 55%, for example, greater than or equal to 60%, greater than or equal to 65%, greater than or equal to 70%, greater than or equal to 75%, greater than or equal to 80%, greater than or equal to 85%, greater than or equal to 90%, greater than or equal to 92%, greater than or equal to 95%, greater than or equal to 97%, greater than or equal to 98%, greater than or equal to 99%, greater than or equal to 99.5%, from greater than 50% to 99%, from greater than 50% to 97%, from greater than 50% to 94%, from greater than 50% to 90%, from 70% to 99.5%, from 70% to 99%, from 70% to 97% from 70% to 94%, from 80% to 99.5%, from 80% to 99%, from 80% to 97%, from 80% to 94%, from 80% to 90%, from 85% to 99.5%, from 85% to 99%, from 85% to 97%, from 88% to 99.9%, 88% to 99.7%, from 88% to 99.5%, from 88% to 99%, from 88% to 98%, from 88% to 97%, from 88% to 95%, from 88% to 94%, from 90% to 99.9%, from 90% to 99.5% from 90% to 99%, from 90% to 97%, from 90% to 95%, from 93% to 99.9%, from 93% to 99.5% from 93% to 99%, or from 93% to 97%, by weight, of the units derived from ethylene; and (b) less than 30 percent, for example, less than 25 percent, or less than 20 percent, less than 18%, less than 15%, less than 12%, less than 10%, less than 8%, less than 5%, less than 4%, less than 3%, less than 2%, less than 1%, from 0.1 to 20%, from 0.1 to 15%, 0.1 to 12%, 0.1 to 10%, 0.1 to 8%, 0.1 to 5%, 0.1 to 3%, 0.1 to 2%, 0.5 to 12%, 0.5 to 10%, 0.5 to 8%, 0.5 to 5%, 0.5 to 3%, 0.5 to 2.5%, 1 to 10%, 1 to 8%, 1 to 5%, 1 to 3%, 2 to 10%, 2 to 8%, 2 to 5%, 3.5 to 12%, 3.5 to 10%, 3.5 to 8%, 3.5% to 7%, or 4 to 12%, 4 to 10%, 4 to 8%, or 4 to 7%, by weight, of units derived from one or more a-olefin comonomers. The comonomer content may be measured using any suitable technique, such as techniques based on nuclear magnetic resonance ("NMR") spectroscopy, and, for example, by 13C NMR analysis as described in U.S. Pat. No. 7,498,282, which is incorporated herein by reference.

Suitable alpha-olefin comonomers typically have no more than 20 carbon atoms. The one or more alpha-olefins may be selected from the group consisting of C3-C20 acetylenically unsaturated monomers and C4-C18 diolefins. For example, the alpha-olefin comonomers may have 3 to 10 carbon atoms, or 3 to 8 carbon atoms. Exemplary alpha-olefin comonomers include, but are not limited to, propylene, 1-butene, 1-pentene, 1-hexene, 1-heptene, 1-octene, 1-nonene, 1-decene, and 4-methyl-1-pentene. The one or more alpha-olefin comonomers may, for example, be selected from the group consisting of propylene, 1-butene, 1-hexene, and 1-octene; or in the alternative, from the group consisting of 1-butene, 1-hexene and 1-octene, or in the alternative, from the group consisting of 1-hexene and 1-octene. In some embodiments, the ethylene/alpha-olefin interpolymer comprises greater than 0 wt. % and less than 30 wt. % of units derived from one or more of 1-octene, 1-hexene, or 1-butene comonomers.

In embodiments described herein, the ethylene/alpha-olefin interpolymer has a density of 0.911 to 0.950 grams/cubic centimeter (g/cc). All individual values and subranges of from 0.911 to 0.950 g/cc are included and disclosed herein. For example, in some embodiments, the polyethylene polymer has a density of 0.911 to 0.945 g/cc, 0.911 to 0.940 g/cc, 0.911 to 0.939 g/cc, or 0.911 to 0.935 g/cc. In other embodiments, the polyethylene polymer has a density of 0.915 to 0.935 g/cc. In further embodiments, the polyethylene polymer has a density of 0.920 to 0.935 g/cc. In even further embodiments, the polyethylene polymer has a density of 0.925 to 0.935 g/cc. Density may be measured according to ASTM D792.

In addition to the density, the ethylene/alpha-olefin interpolymer has a Brookfield viscosity of less than or equal to 50,000 centipoise (cP). All individual values and subranges of less than or equal to 50,000 cP are included and disclosed herein. For example, in some embodiments, the ethylene/alpha-olefin interpolymer has a Brookfield viscosity of less than or equal to 45,000 cP, less than or equal to 40,000 cP, or less than or equal to 35,000 cP. In other embodiments, ethylene/alpha-olefin interpolymer has a Brookfield viscosity of from 5,000 cP to 50,000 cP, from 5,000 cP to 45,000 cP, or 5,000 cP to 40,000 cP.

In addition to the density and Brookfield viscosity, the ethylene/alpha-olefin interpolymer has a molecular weight distribution ($M_{w,cc}/M_{n,cc}$) of from 1.8 to 3.5. Molecular weight distribution can be described as the ratio of weight-average molecular weight ($M_{w,cc}$) to number-average molecular weight ($M_{n,cc}$) (i.e., $M_{w,cc}/M_{n,cc}$), and can be measured by gel permeation chromatography (GPC) techniques. All individual values and subranges of from 1.8 to 3.5 are included and disclosed herein. For example, in some embodiments, the ethylene/alpha-olefin interpolymer has a molecular weight distribution ($M_{w,cc}/M_{n,cc}$) of from 1.9 to 3.5 or 2.0 to 3.5. In other embodiments, the ethylene/alpha-olefin interpolymer has a molecular weight distribution ($M_{w,cc}/M_{n,cc}$) of from 1.8 to 3.0, 1.9 to 3.0, or 2.0 to 3.0. In further embodiments, the ethylene/alpha-olefin interpolymer has a molecular weight distribution ($M_{w,cc}/M_{n,cc}$) of from 1.8 to 2.8, 1.9 to 2.8, or 2.0 to 2.8.

In addition to the density, Brookfield viscosity, and molecular weight distribution, the ethylene/alpha-olefin interpolymer may have an $M_{z,cc}/M_{n,cc}$ of less than 4.0. $M_{z,cc}$ can be described as the z average molecular weight. All individual values and subranges of less than 4.0 are included and disclosed herein. For example, in some embodiments, the ethylene/alpha-olefin interpolymer has a $M_{z,cc}/M_{n,cc}$ of less than 3.5. In other embodiments, the ethylene/alpha-olefin interpolymer has a M of from 2.5 to 4.0 or from 2.5 to 3.5.

In addition to the density, Brookfield viscosity, molecular weight distribution, and $M_{z,cc}/M_{n,cc}$, the ethylene/alpha-olefin interpolymer may have a weight fraction (w) of molecular weight greater than $10^5$ g/mole, based on the total weight of interpolymer, as determined by conventional gel permeation chromatography, of less than 2.5%. All individual values and subranges of less than 2.5% are included and disclosed herein. For example, in some embodiments, the ethylene/alpha-olefin interpolymer has a weight fraction (w) of molecular weight greater than $10^5$ g/mole, based on the total weight of interpolymer, as determined by conventional gel permeation chromatography, of less than 1.0%.

In addition to the density, Brookfield viscosity, molecular weight distribution, $M_{z,cc}/M_{n,cc}$, and weight fraction (w) of molecular weight greater than $10^5$ g/mole, the ethylene/alpha-olefin interpolymer may have a comonomer distribution breadth index (CDBI) of greater than or equal to 50%. All individual values and subranges of greater than or equal to 50% are included and disclosed herein. For example, in some embodiments, the ethylene/alpha-olefin interpolymer has a CDBI of greater than or equal to 55%, greater than or equal to 60%, greater than or equal to 65%, greater than or equal to 70%, or greater than or equal to 75%. In other embodiments, the ethylene/alpha-olefin interpolymer has a CDBI ranging from 50% to 98%, 50% to 97%, 55% to 98%, 55% to 97%, 60% to 98%, 60% to 97%, 70% to 98%, 70% to 97%, 75% to 98%, or 75% to 97%. In further embodiments, the ethylene/alpha-olefin interpolymer has a CDBI ranging from 50% to 85%, 55% to 85%, 60% to 85%, 60% to 80%, 65% to 80%, or 70% to 80%.

In addition to the density, Brookfield viscosity, molecular weight distribution, $M_{z,cc}/M_{n,cc}$ weight fraction (w) of molecular weight greater than $10^5$ g/mole, and CDBI, the ethylene/alpha-olefin interpolymer may have a highest DSC temperature crystallization peak, Tc, of from 80° C. to 110° C. All individual values and subranges of from 80° C. to 110° C. are included and disclosed herein. For example, in some embodiments, the ethylene/alpha-olefin interpolymer has a Tc of from 80° C. to 105° C., from 85° C. to 105° C., or from 90° C. to 105° C. In other embodiments, the ethylene/alpha-olefin interpolymer has a Tc of from 95° C. to 105° C. The highest DSC temperature crystallization peak is determined using the differential scanning calorimetry (DSC) method outlined below.

In addition to the density, Brookfield viscosity, molecular weight distribution, $M_{z,cc}/M_{n,cc}$ weight fraction (w) of molecular weight greater than $10^5$ g/mole, CDBI, and Tc, the ethylene/alpha-olefin interpolymer may have a temperature differential between the highest DSC temperature melting peak (Tm) and the highest DSC temperature crystallization peak (Tc), ΔTm-Tc, of less than 16° C. All individual values and subranges of less than 16° C. are included and disclosed herein. For example, in some embodiments, the ethylene/alpha-olefin interpolymer may have a ΔTm-Tc of less than 15° C. In other embodiments, the ethylene/alpha-olefin interpolymer may have a ΔTm-Tc of less than 12° C. The highest DSC temperature melting peak (Tm) is determined using the differential scanning calorimetry (DSC) method outlined below.

In embodiments herein, the ethylene/alpha-olefin interpolymer may be prepared in a solution polymerization process using one or more conventional reactors e.g. loop reactors, isothermal reactors, plug flow reactors, and/or stirred tank reactors in parallel, series, and/or any combinations thereof in continuous or batch mode to produce olefin based polymers, e.g. ethylene polymers or propylene polymers. The solution phase polymerization process may occur in one or more well-stirred reactors, such as one or more loop reactors or one or more isothermal reactors, at a temperature in the range of from 100 to 300° C.; for example, from 120 to 190° C., and at pressures in the range of from 300 to 1,000 psig; for example, from 400 to 750 psig. The residence time in solution phase polymerization process is typically in the range of from 2 to 30 minutes; for example, from 5 to 20 minutes. Ethylene (monomer), solvent, hydrogen, one or more catalyst systems, and one or more comonomers are fed continuously to the reactor. Exemplary solvents include, but are not limited to, isoparaffins and naphthinics. For example, such solvents are commercially available under the name ISOPAR E from ExxonMobil Chemical Co., Houston, Texas or under the name SBP 100/140 from Shell Chemicals Europe. The effluent from the polymerization reactor (containing solvent, monomer, comonomer, hydrogen, catalyst components, and molten polymer) exits the reactor and enters a zone where it is contacted with a deactivating agent and, optionally, an acid scavenging agent (such as calcium stearate and the accompanying water of hydration) to stop the reaction and scavenge hydrogen chloride. In addition, various additives, such as antioxidants, can be added at this point. The stream then goes through another set of static mixing elements, such as Kenics helical static mixing elements, to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a multi-stage separation and devolatilization system where the polymer is removed from the solvent, hydrogen, and unreacted monomer and comonomer. Impurities are removed from the recycled, lower boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can also have some hydrogen which is then fortified with fresh hydrogen.

In some embodiments, the ethylene/alpha-olefin interpolymers may be prepared using a catalyst composition via a solution phase polymerization process in a loop reactor in accordance with the following procedure. All raw materials (ethylene, and one or more alpha-olefin comonomers, such as hexene or octene) and the process solvent (an isoparaffinic solvent, for example ISOPAR E) are purified with molecular sieves before introduction into the reaction environment. Hydrogen is supplied as a high purity grade and is not further purified. The reactor monomer feed (ethylene) stream is pressurized via a mechanical compressor to a pressure that is above the reaction pressure, e.g. 750 psig. The solvent and comonomer (one or more alpha-olefin comonomer, such as hexene or octene) feed is pressurized via a mechanical positive displacement pump to a pressure that is above the reaction pressure, e.g. 750 psig. The individual catalyst components can be manually batch diluted to specified component concentrations with purified solvent (ISOPAR E) and pressurized to a pressure that is above the reaction pressure, e.g. 750 psig. All reaction feed flows can be measured with mass flow meters and independently controlled with computer automated valve control systems.

The continuous solution polymerization reactor may consist of a liquid full, non-adiabatic, isothermal, circulating, loop. Independent control of all fresh solvent, monomer, comonomer, hydrogen, and catalyst component feeds is possible. The combined solvent, monomer, comonomer and hydrogen feed is temperature controlled to anywhere between 5° C. to 50° C. and typically 40° C. by passing the feed stream through a heat exchanger. The fresh comonomer feed to the polymerization reactor is aligned to add comonomer to the recycle solvent. The total fresh feed to the polymerization reactor is injected into the reactor at, for example, two locations roughly with equal reactor volumes between each injection location. The fresh feed is controlled typically with each injector, for example, receiving half of the total fresh feed mass flow. The catalyst components are injected into the polymerization reactor through, for example, a specially designed injection inlet device and are combined into one mixed procatalyst/cocatalyst feed stream prior to injection into the reactor. The procatalyst component feed is computer controlled to maintain the reactor monomer concentration at a specified target. The cocatalyst component is fed based on calculated specified molar ratios to the procatalyst component Immediately following each fresh injection location (either feed or catalyst), the feed streams are mixed with the circulating polymerization reactor contents with static mixing elements, such as Kenics helical static mixing elements. The contents of the reactor are continuously circulated through heat exchangers responsible for removing much of the heat of reaction and with the temperature of the coolant side responsible for maintaining an isothermal reaction environment at the specified temperature. Circulation around the reactor loop can be provided by a screw pump. The effluent from the polymerization reactor (containing solvent, monomer, comonomer, hydrogen, catalyst components, and molten polymer) exits the reactor and enters a zone where it is contacted with a deactivating and, optionally, an acid scavenging agent (e.g., calcium stearate and the accompanying water of hydration) to stop the reaction and scavenge hydrogen chloride. In addition, various additives such as antioxidants can be added at this point. The stream then goes through another set of static mixing elements, such as Kenics helical static mixing elements to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a two stage separation and devolatilization system where the polymer is removed from the solvent, hydrogen, and unreacted monomer and comonomer.

Impurities are removed from the recycled low boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can still have some hydrogen which is then fortified with fresh hydrogen.

In other embodiments, the ethylene/alpha-olefin interpolymer may be prepared using one or more catalyst systems suitable for polymerizing ethylene and one or more alpha-olefin comonomers via a solution phase polymerization process in two adiabatic stirred-tank reactors, linked together in series in accordance to the following procedure. The ethylene monomer and one or more alpha-olefin comonomers, and hydrogen are combined with a solvent, e.g. an isoparaffinic solvent, such as ISOPAR E. Impurities such as water, carbon dioxide, sulfurous compounds are removed from the feed streams, and the feed streams are cooled to temperature in the range of 5° C. to 60° C., for example, approximately 13° C., before entering the reactor. The majority, approximately from 85 to 90 percent, of the reaction may occur in the first adiabatic stirred-tank reactor. The mixing may be achieved via circulating the polymer/procatalyst/cocatalyst/solvent/ethylene/one or more alpha-olefin comonomers/hydrogen solution with one or more agitators equipped with mixing blades. The feed (ethylene/one or more alpha-olefin comonomers/solvent/hydrogen) may, for example, enter the reactor from the bottom and the procatalyst/cocatalyst may, for example, enter the reactor separately from the feed and also from the bottom. The first reactor temperature is in the range of from 120° C. to 190° C., for example, approximately 175° C., and the reactor pressure is in the range of from 400 psig to 1,000 psig, for example, approximately 500 psig. The temperature of the second reactor, in series with the first reactor, increases to a temperature in the range of from 175° C. to 210° C., for example, approximately 202° C. with approximately from 10 to 15 percent of the remaining reaction occurring and no additional catalyst or monomers are added. The average reactor residence time is in the range of from 2 to 30 minutes, for example, approximately 8 minutes per adiabatic stirred-tank reactor prior to termination post-reactor by a fluid specially designed for that purpose.

The effluent from the polymerization reactor (containing solvent, monomer, comonomer, hydrogen, catalyst components, and molten polymer) exits the reactor and enters a zone where it is contacted with a deactivating and optionally an acid scavenging agent (e.g., calcium stearate and the accompanying water of hydration) to stop the reaction and scavenge hydrogen chloride. In addition, various additives such as antioxidants can be added at this point. The stream then goes through another set of static mixing elements, such as Kenics helical static mixing elements to evenly disperse the catalyst kill and additives. The effluent (containing solvent, monomer, comonomer, hydrogen, catalyst components, and molten polymer) passes through a heat exchanger to raise the stream temperature in preparation for separation of the polymer from the other lower boiling reaction components. The stream then passes through a pressure let down control valve, which is responsible for maintaining the pressure of the reactor at a specified target. The stream then enters a two stage separation and devolatilization system where the polymer is removed from the solvent, hydrogen, and unreacted monomer and comonomer. Impurities are removed from the recycled lower boiling reaction components before entering the reactor again. The separated and devolatilized polymer melt is pumped through a heat exchanger to lower the stream temperature to a temperature in the range of less than 200° C., for example less than 170° C., or in the range of from 50 to 110° C.; thereby producing a cooled polymer melt. Subsequently, the cooled polymer melt is pumped through a die specially designed for underwater pelletization, cut into uniform solid pellets, dried, and transferred into a hopper. After validation of initial polymer properties, the solid polymer pellets are transferred to storage devices. The portions removed in the devolatilization step may be recycled or destroyed. For example, most of the solvent is recycled back to the reactor after passing through purification beds. This recycled solvent can still have unreacted co-monomer in it that is fortified with fresh co-monomer prior to re-entry to the reactor. This recycle solvent can still have some hydrogen which is then fortified with fresh hydrogen.

Bicomponent Fibers/Meltblown Nonwoven

The bicomponent fibers described herein have a shear viscosity ratio of the first composition to the second composition of less than 2.0. All individual values and subranges of less than 2.0 are included and disclosed herein. For example, in some embodiments, the bicomponent fibers have a shear viscosity ratio of the first composition to the second composition of less than 1.5, less than 1.0, less than 0.95, or less than 0.90. In other embodiments, the bicomponent fibers have a shear viscosity ratio of the first composition to the second composition of 0.5-2.0, 0.5-1.5, or 0.5-1.0. In further embodiments, the bicomponent fibers have a shear viscosity ratio of the first composition to the second composition of 0.75-2.0, 0.75-1.5, or 0.75-1.0.

In some embodiments herein, the bicomponent fiber has a sheath/core structures. The first region may comprise the core and the second region may comprise the sheath. Alternatively, the first region may comprise the sheath, and the second region may comprise the core.

The meltblown nonwoven is formed from a bicomponent fiber by extruding the first composition and the second composition through a plurality of fine, usually circular, die capillaries as molten threads or filaments into converging high velocity gas streams (e.g. air) which function to attenuate the threads or filaments to reduced diameters. Thereafter, the filaments or threads are carried by the high velocity gas streams and deposited on a collecting surface to form a nonwoven web of randomly dispersed meltblown bicomponent fibers with average diameters generally smaller than 10 microns. The terms "nonwoven," "nonwoven web," and "nonwoven fabric" are used herein interchangeably. "Nonwoven" refers to a web or fabric having a structure of individual fibers or threads which are randomly interlaid, but not in an identifiable manner as is the case for a knitted fabric.

The meltblown nonwoven may be used in a composite structure. The composite structure may further comprise one or more spunbond nonwovens. As used herein, "spunbond" refers to fibers formed by extruding a molten thermoplastic polymer composition as filaments through a plurality of fine, usually circular, die capillaries of a spinneret with the diameter of the extruded filaments then being rapidly reduced and thereafter depositing the filaments onto a collecting surface to form a web or fabric of randomly dispersed spunbond fibers with average diameters generally between about 7 and about 30 microns. The spunbond fibers may be bicomponent or monocomponent fibers. The monocomponent fibers comprise polyethylene. The bicomponent fibers may have a sheath/core structure where the sheath comprises polyethylene and the core comprises polypropylene. Of course, other configurations of bicomponent fibers may be used, such as, a side by side arrangement, a pie arrangement, or an "islands-in-the sea" arrangement.

In some embodiments, the composite has a SaMbSc configuration, wherein S is a spunbond nonwoven, M is the meltblown nonwoven as described herein, and a, b, and c are the number of layers, and are independent integers ranging from 1 to 5. For example, the composite may have a SMS (where a=1, b=1, and c=1), SMMS (where a=1, b=2, and c=1), SSMSS (where a=2, b=1, and c=2), SMMMS (where a=1, b=3, and c=1), SMMSS (where a=1, b=3, and c=2), or other configurations, as "a,", "b," and "c" are independent of each other.

Test Methods

Density

Density is measured in accordance with ASTM D-792, and expressed in grams/cubic centimeter (g/cc).

Melt Index (I2)/Melt Flow Rate

Melt index (I2) may be measured in accordance with ASTM 1238 at 190 Celsius and 2.16 kg, and is expressed in grams eluted/10 minutes (g/10 min). Melt Flow Rate is measured in accordance with ISO 1133 at 230 Celsius and 2.16 kg.

Brookfield Viscosity

Brookfield Viscosity is measured with a DV-II Pro Extra Viscometer. The instrument uses the Rheocalc V3.3 software which gives a great control and precision of the viscometer. 8 grams of sample is used when using the SC4-31 spindle size. Test temperature is 350° F.°. Adequate spindle speed is applied so that the torque is between 40% to 70% level. Viscosity data is recorded after 20 minutes when a stable viscosity reading is obtained.

Complex Viscosity

Dynamic frequency sweep measurements are conducted on an ARES-2 Rheometer at 210° C. with 2 mm compression molded plaques. Each material is vacuum dried for 2 hours at 80° C., then compression molded at 190° C. and cooled down by the aid of cooling cassettes (to avoid crystallization behavior of the PP material). The applied strain is in a range of 10-20%. The plates diameter is 50 mm. The applied frequency range is between 0.1-100 s$^{-1}$. The plates gap is 1 mm. All measurements are conducted under nitrogen to avoid material degradation.

Conventional GPC

Conventional GPC is obtained by high temperature gel permeation chromatography (GPC) equipment (PolymerChar, Spain). The IR5 detector ("measurement channel") is used as a concentration detector. GPCOne software (PolymerChar, Spain) is used to calculate the z-average (Mz,cc), weight-average (Mw,cc), and number-average (Mn,cc) molecular weight of the polymer and to determine the MWD (=Mw,cc/Mn,cc). The method uses three 10 micron PL gel mixed B columns (Agilent Technologies, column dimension 100×7.6 mm) or four 20 micron PL gel mixed A columns (Agilent Technologies, column dimension 100×7.6 mm) operating at a system temperature of 150° C. Samples are prepared at a 2 mg/mL concentration in 1,2,4-trichlorobenzene solvent containing 200 part per million of antioxidant butylated hydroxytoluene (BHT) for 3 hours at 160° C. with a gentle shaking by autosampler (PolymerChar, Spain). The flow rate is 1.0 mL/min, the injection size is 200 microliters. GPCOne software is used to calculate the plate count. The chromatographic system must have a minimum of 22,000 plates.

The GPC column set is calibrated by running at least 20 narrow molecular weight distribution polystyrene standards. The calibration uses a third order fit for the system with three 10 micron PL gel mixed B columns or a fifth order fit for the system with four 20 micron PL gel mixed A columns. The molecular weight (MW) of the standards range from 580 g/mol to 8,400,000 g/mol, and the standards are contained in 6 "cocktail" mixtures. Each standard mixture has approximately a decade of separation between individual molecular weights. The standard mixtures are purchased from Agilent Technologies. The polystyrene standards are prepared at "0.025 g in 50 mL of solvent" for molecular weights equal to, or greater than, 1,000,000 g/mol, and at "0.05 g in 50 mL of solvent" for molecular weights less than 1,000,000 g/mol. The polystyrene standards are dissolved at 80° C., with gentle agitation, for 30 minutes. The narrow standards mixtures are run first, and in order of decreasing highest molecular weight component, to minimize degradation. The polystyrene standard peak molecular weights are converted to polyethylene molecular weights using Equation (1) (as described in Williams and Ward, J. Polym. Sci., Polym. Letters, 6, 621 (1968)):

$$MW_{PE} = A \times (MW_{PS})^B \qquad \text{(Eq. 1)}$$

where MW is the molecular weight of polyethylene (PE) or polystyrene (PS) as marked, and B is equal to 1.0. It is known to those of ordinary skill in the art that A may be in a range of about 0.38 to about 0.44 such that the A value yields 52,000 MWPE for Standard Reference Materials (SRM) 1475a. Use of this polyethylene calibration method to obtain molecular weight values, such as the molecular weight distribution (MWD or Mw/Mn), and related statistics, is defined here as the modified method of Williams and Ward. The number-average molecular weight, the weight-average molecular weight, and the z-average molecular weight are calculated from the following equations.

$$M_{n,cc} = \sum w_i / \sum (w_i / M_{cc,i}) \qquad \text{(Eq. 2)}$$

$$M_{w,cc} = \sum w_i M_{cc,i} \qquad \text{(Eq. 3)}$$

$$M_{z,cc} = \sum (w_i M_{cc,i}^2) / \sum (w_i M_{cc,i}) \qquad \text{(Eq. 4)}$$

where $M_{n,cc}$, $M_{w,cc}$, and $M_{z,cc}$ (in g/mole) are the number-, weight-, and z-average molecular weight obtained from the conventional calibration, respectively. $w_i$ is the weight fraction of the polyethylene molecules eluted at retention volume $V_i$. $M_{cc,i}$ is the molecular weight (in g/mole) of the polyethylene molecules eluted at retention volume $V_i$ obtained using the conventional calibration (see Equation (1)).

The chromatographic peaks should be set to include area marking a significant visible departure from baseline when the chromatogram is viewed at 20 percent peak height. The baseline should not be integrated to less than 100 polyethylene-equivalent molecular weight and care must be used to account for anti-oxidant mismatch from the prepared sample and the chromatographic mobile phase. Referring to FIG. 1, depicted is the proper baseline and integration limit sets for a sample that exhibits a clear separate anti-oxidant peak.

Figure 2:
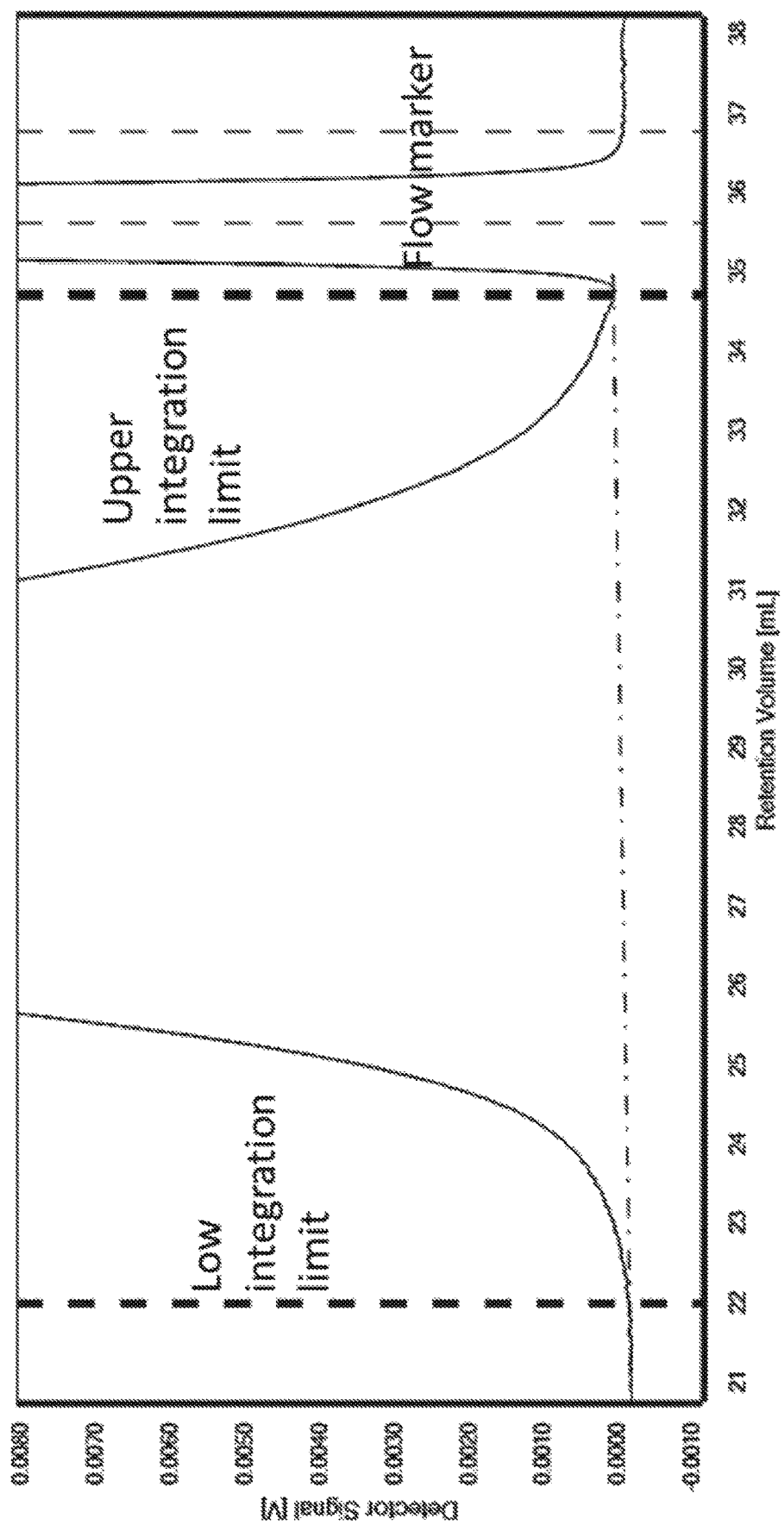
FIG. 2 graphically depicts a chromatogram plot of the detector signal (V) versus retention volume (ml) and the proper baseline and integration limits sets for a sample that shows continuity towards 100 polyethylene-equivalent molecular weight.

Use of a decane flow rate marker is shown in the IR5 chromatogram (see FIGS. 1 and 2). At no point should the baseline (response) Y-value difference between the start and the end of the baseline be greater than 3 percent of the integrated peak height of the chromatogram. In such a case, the chromatographic sample must be handled through proper matching of the sample and mobile phase antioxidant.

Referring to FIG. 2, depicted is the proper baseline and integration limits sets for a sample that shows continuity towards 100 polyethylene-equivalent molecular weight. At no point should the end integration limit be set lower than 100 polyethylene-equivalent molecular weight.

w (wt. fraction greater than $10^5$ g/mole) is calculated according the MWD curve (wi versus log Mcc, i) obtained from GPCOne software according to Equation (5)

$$w = \int_{logM_{cc,i}=5}^{logM_{cc,i}=7} w_i d\log M_{cc,i} / \int_{logM_{cc,i}=2}^{logM_{cc,i}=7} w_i d\log M_{cc,i} \quad (Eq. 5)$$

Triple Detector Gel Permeation Chromatography (TDGPC)—Light Scattering GPC

For the GPC techniques used herein (Light Scattering GPC), a Triple Detector Gel Permeation Chromatography (3D-GPC or TDGPC) system is used. This system consists of a PolymerChar (Valencia, Spain) GPC-IR High Temperature Chromatograph, equipped with a Precision Detectors (Now Agilent Technologies) 2-angle laser light scattering (LS) detector Model 2040, an IR5 infra-red detector, and 4-capillary viscometer detector from PolymerChar. Data collection and data processing are performed using PolymerChar "Instrument Control" and GPCOne software. The system is also equipped with an on-line solvent degassing device from Agilent Technologies (CA, USA). GPCOne software is used to calculate the plate count. The chromatographic system must have a minimum of 22,000 plates.

The eluent from the GPC column set flows through each detector arranged in series, in the following order: IR5 detector, LS detector, then the Viscometer detector. The systematic approach for the determination of multi-detector offsets is performed in a manner consistent with that published by Balke, Mourey, et al. (Mourey and Balke, Chromatography Polym., Chapter 12, (1992)) (Balke, Thitiratsakul, Lew, Cheung, Mourey, Chromatography Polym., Chapter 13, (1992)), optimizing triple detector log (MW and intrinsic viscosity) results from using a broad polyethylene standard, as outlined below.

Four 20-micron mixed-pore-size packing ("Mixed A", Agilent Technologies) are used for the separation. The PolymerChar Autosampler oven compartment is operated at 160° C. with low speed shaking for 3 hours, and the column compartment is operated at 150° C. The samples are prepared at a concentration of "2 milligrams per milliliter." The chromatographic solvent and the sample preparation solvent is 1,2,4-trichlorobenzene (TCB) containing "200 ppm of 2,6-di-tert-butyl-4methylphenol (BHT)." The solvent is sparged with nitrogen. The injection volume is 200 microliters. The flow rate through the GPC is set at 1 ml/minute.

For the LS GPC, the Precision Detector PDI2040 detector Model 2040 15° angle is used. The molecular weight data is obtained in a manner consistent with that published by Zimm (Zimm, B H, J Chem. Phys., 16, 1099 (1948)) and Kratochvil (Kratochvil, P., Classical Light Scattering from Polymer Solutions, Elsevier, Oxford, NY (1987)), which are incorporated herein by reference. The overall injected concentration, used in the determination of the molecular weight, is obtained from the mass detector (IR5) area, and the mass detector constant, derived from a suitable linear polyethylene homopolymer, or one of the polyethylene standards of known weight-average molecular weight. The calculated molecular weights are obtained using a light scattering constant, derived from one or more of the polyethylene standards mentioned below, and a refractive index concentration coefficient, dn/dc, of 0.104. Generally, the mass detector response and the light scattering constant should be determined from a linear standard with a molecular weight in excess of about 50,000 g/mole. The viscometer calibration can be accomplished using the methods described by the manufacturer, or, alternatively, by using the published values of suitable linear standards, such as Standard Reference Materials (SRM) 1475a (available from National Institute of Standards and Technology (NIST)). The chromatographic concentrations are assumed low enough to eliminate addressing 2nd viral coefficient effects (concentration effects on molecular weight).

With 3D-GPC, absolute weight-average molecular weight ("$M_{w,abs}$") and absolute z-average molecular weight ("$M_{z,abs}$") is determined using Equations (6) and (7) below, wherein the $M_{w,abs}$ is obtained using the "peak area" method (after detector calibration relating areas to mass and mass—molecular weight product) for higher accuracy and precision. The "LS.Area" and the "Concentration.Area" are generated by the chromatograph/detectors combination.

$$M_{w,abs} = \frac{\sum C_i M_{abs,i}}{\sum C_i} = \frac{\sum LS_i}{\sum C_i} = \frac{LS.Area}{Concentration.Area} \quad (Eq. 6)$$

$$M_{z,abs} = \sum (w_i M_{abs,i}^2) / \sum (w_i M_{abs,i}) \quad (Eq. 7)$$

where $C_i$ is the concentration of the polyethylene molecules in the eluent at the retention volume $V_i$, $M_{abs,i}$ is the absolute molecular weight of the polyethylene molecules at the retention volume $V_i$, $LS_i$ is the response of the light scattering detector at the retention volume $V_i$, $\Sigma LS_i$ (LS.Area) is the total response of the light scattering, and the $\Sigma Ci$ (Concentration.Area) is the total concentration.

The weight-average molecular weight by light scattering (LS) using Equation (6) is commonly referred to as "absolute weight-average molecular weight" or "$M_{w,\ abs}$." The $M_{n,cc}$, $M_{w,cc}$, and $M_{z,cc}$ from Equation (2, 3, 4) use conventional GPC molecular weight calibration curve ("conventional calibration") and $M_{w,cc}$ is often referred to as "polymer chain backbone molecular weight," "conventional weight-average molecular weight," and "$M_{w,cc}$".

Differential Scanning Calorimetry (DSC)

DSC was used to measure the melting and crystallization behavior of a polymer over a wide range of temperatures. For example, the TA Instruments Q1000 DSC, equipped with an RCS (refrigerated cooling system) and an autosampler was used to perform this analysis. During testing, a nitrogen purge gas flow of 50 ml/min was used. Each sample was melt pressed into a thin film at about 175° C.; the melted sample was then air-cooled to room temperature (approx.

25° C.). The film sample was formed by pressing a "0.1 to 0.2 gram" sample at 175° C. at 1,500 psi, and 30 seconds, to form a "0.1 to 0.2 mil thick" film. A 3-10 mg, 6 mm diameter specimen was extracted from the cooled polymer, weighed, placed in a light aluminum pan (ca 50 mg), and crimped shut. Analysis was then performed to determine its thermal properties.

The thermal behavior of the sample was determined by ramping the sample temperature up and down to create a heat flow versus temperature profile. First, the sample was rapidly heated to 180° C., and held isothermal for five minutes, in order to remove its thermal history. Next, the sample was cooled to −40° C., at a 10° C./minute cooling rate, and held isothermal at −40° C. for five minutes. The sample was then heated to 150° C. (this is the "second heat" ramp) at a 10° C./minute heating rate. The cooling and second heating curves were recorded. The cool curve was analyzed by setting baseline endpoints from the beginning of crystallization to −20° C. The heat curve was analyzed by setting baseline endpoints from −20° C. to the end of melt. The values determined were highest peak melting temperature ($T_m$), highest peak crystallization temperature ($T_c$), heat of fusion ($H_f$) (in Joules per gram), and the calculated % crystallinity for polyethylene samples using: % Crystallinity=(($H_f$)/(292 J/g))×100. The heat of fusion ($H_f$) and the highest peak melting temperature were reported from the second heat curve. The highest peak crystallization temperature is determined from the cooling curve.

Crystallization Elution Fractionation (CEF) Method

Comonomer distribution analysis, also commonly called short chain branching distribution (SCBD), is measured with Crystallization Elution Fractionation (CEF) (PolymerChar, Spain) (Monrabal et al, Macromol. Symp. 257, 71-79 (2007), which is incorporated herein by reference) equipped with IR-4 detector (PolymerChar, Spain) and two angle light scattering detector Model 2040 (Precision Detectors, currently Agilent Technologies). IR-4 or IR-5 detector is used. A 10 or 20 micron guard column of 50×4.6 mm (PolymerLab, currently Agilent Technologies) is installed just before the IR-4 detector or IR-5 detector in the detector oven. Ortho-dichlorobenzene (ODCB, 99% anhydrous grade) and 2,5-di-tert-butyl-4-methylphenol ("BHT", catalogue number B1378-500G, batch number 098K0686) from Sigma-Aldrich are obtained. ODCB is distilled before use. Silica gel 40 (particle size 0.2-0.5 mm, catalogue number 10181-3) from EMD Chemicals is also obtained. The silica gel is dried in a vacuum oven at 160° C. for about two hours before use. Eight hundred milligrams of BHT and five grams of the silica gel are added to two liters of ODCB. ODCB can be also dried by passing through a column or columns packed with silica gel. For the CEF instrument equipped with an autosampler with $N_2$ purging capability, Silica gel 40 is packed into two 300×7.5 mm GPC size stainless steel columns and the Silica gel 40 columns are installed at the inlet of the pump of the CEF instrument to dry ODCB; and no BHT is added to the mobile phase. This "ODCB containing BHT and silica gel" or ODCB dried with silica gel 40 is now referred to as "ODCB." This ODCB is sparged with dried nitrogen (N2) for one hour before use. Dried nitrogen is such that is obtained by passing nitrogen at <90 psig over $CaCO_3$ and 5 Å molecular sieves. The resulting nitrogen should have a dew point of approximately −73° C. Sample preparation is done with autosampler at 4 mg/ml (unless otherwise specified) under shaking at 160° C. for 2 hours. The injection volume is 300 μl. The temperature profile of CEF is: crystallization at 3° C./min from 110° C. to 30° C., the thermal equilibrium at 30° C. for 5 minutes (including Soluble Fraction Elution Time being set as 2 minutes), elution at 3° C./min from 30° C. to 140° C. The flow rate during crystallization is 0.052 ml/min. The flow rate during cooling step is 0.052 mL/min. The flow rate during elution is 0.50 ml/min. The data is collected at one data point/second. The CEF column is packed with glass beads at 125 μm±6% (MO-SCI Specialty Products) with ⅛ inch stainless tubing according to U.S. Pat. No. 8,372,931, which is incorporated herein by reference. The column outside diameter (OD) is ⅛ inch. The critical parameters needed to duplicate the method include the column internal diameter (ID), and column length (L). The choice of ID and L must be such that when packed with the 125 μm diameter glass beads, the liquid internal volume is 2.1 to 2.3 mL. If L is 152 cm, then ID must be 0.206 cm and the wall thickness must be 0.056 cm. Different values for L and ID can be used, as long as the glass bead diameter is 125 μm and the internal liquid volume is between 2.1 and 2.3 mL. Column temperature calibration is performed by using a mixture of NIST Standard Reference Material Linear polyethylene 1475a (1.0 mg/ml) and Eicosane (2 mg/ml) in ODCB. CEF temperature calibration consists of four steps: (1) Calculating the delay volume defined as the temperature offset between the measured peak elution temperature of Eicosane minus 30.00° C.; (2) Subtracting the temperature offset of the elution temperature from CEF raw temperature data. It is noted that this temperature offset is a function of experimental conditions, such as elution temperature, elution flow rate, etc.; (3) Creating a linear calibration line transforming the elution temperature across a range of 30.00° C. and 140.00° C. so that NIST linear polyethylene 1475a has a peak temperature at 101.0° C., and Eicosane has a peak temperature of 30.0° C.; (4) For the soluble fraction measured isothermally at 30° C., the elution temperature is extrapolated linearly by using the elution heating rate of 3° C./min. The reported elution peak temperatures are obtained such that the observed comonomer content calibration curve agrees with those previously reported in U.S. Pat. No. 8,372,931, which is incorporated herein by reference. CEF data is processed by GPCOne software (PolymerChar, Spain).

Comonomer Distribution Breadth Index (CDBI)

The CDBI is defined as the weight percent of the polymer molecules having a co-monomer content within 50 percent of the median total molar co-monomer content (as reported in WO 93/03093, which is incorporated herein by reference). The CDBI of polyolefins can be conveniently calculated from the short chain branching distribution (SCBD) data obtained from the techniques known in the art, such as, for example, temperature rising elution fractionation ("TREF") as described, for example, by Wild, et al., Journal of Polymer Science, Poly. Phys. Ed., Vol. 20, 441 (1982); L. D. Cady, "The Role of Comonomer Type and Distribution in LLDPE Product Performance," SPE Regional Technical Conference, Quaker Square Hilton, Akron, OH, 107-119 (Oct. 1-2, 1985); or in U.S. Pat. No. 4,798,081 (Hazlitt, et al.) and U.S. Pat. No. 5,008,204 (Stehling), all of which are incorporated herein by reference.

Herein, CDBI is calculated according to the following steps with the SCBD measured by CEF:

(A) Obtain a weight fraction at each temperature (T) (wT(T)) from 20.0° C. to 119.0° C. with a temperature step increase of 0.200° C. from CEF according to the equation $$\int_{20.0}^{119.9} wT(T)dT = 1.00$$

(B) Calculate the median temperature ($T_{median}$) at cumulative weight fraction of 0.500 (50%) including soluble fraction. The cumulative weight fraction for the entire elution temperature range (generally between 20.0 to 120.0° C.) is normalized as 1.00

(C) Calculate the corresponding median total comonomer content in mole % ($C_{median}$) at the median temperature ($T_{median}$) by using comonomer content calibration versus elution temperature (D) Construct a comonomer content calibration curve by using a series of reference materials (ethylene-octene copolymers) with known amount of comonomer content, i.e., eleven reference materials with narrow comonomer distribution (mono-modal comonomer distribution in CEF from 35.0 to 119.0° C.) with weight-average Mw (by conventional GPC) of 35,000 to 115,000 (measured via conventional GPC) at a comonomer content ranging from 0.0 mole % to 7.0 mole % are analyzed with CEF at the same experimental conditions specified in CEF experimental sections. The comonomer content of the reference materials is determined using 13C NMR analysis in accordance with techniques described, for example, in U.S. Pat. No. 5,292,845 (Kawasaki, et al.) and by J. C. Randall in Rev. Macromol. Chem. Phys., C29, 201-317, which are incorporated herein by reference.

(E) Calculate comonomer content calibration by using the peak temperature ($T_p$) of each reference material and its comonomer content; The calibration is calculated from each reference material as shown in Formula 4, FIG. 4, wherein: $R^2$ is the correlation constant;

$$\ln(1 - \text{comonomer content}) = -\frac{207.26}{273.12 + T} + 0.5533$$

$$R^2 = 0.997$$

(F) Calculate CDBI as the total weight percentage with a comonomer content ranging from $0.5*C_{median}$ to $1.5*C_{median}$. If the density of the polymer is above 0.94, CDBI is thus defined as 100% (see WO1993003093 A1, which is incorporated herein by reference).

Air Permeability

Air permeability is tested in accordance with EDANA WSP 70.1 using a FX 3300 Air Permeability Tester III manufactured by TexTest Instruments, and expressed in cubic feet per minute. Test pressure is 200 Pa and test area is 20 cm².

EXAMPLES

Materials

Polymer 1 (Poly. 1) is a polypropylene homopolymer (Borflow™ HL512FB), available from Borealis AG (Vienna, Austria), having a melting point of 158° C. (ISO 11357-3) and a melt flow rate (MFR) of 1200 g/10 minute (ISO 1133, 230° C., 2.16 kg). Additional characteristics of the polymer are provided in the tables below.

Polymer 2 (Poly. 2) is an ethylene/alpha-olefin interpolymer, available as DNDA 1082 NT7 from The Dow Chemical Company (Midland, MI). Additional characteristics of the polymer are provided in the tables below.

Production of the Inventive Polymer

The inventive ethylene/alpha-olefin interpolymer was prepared according to the following process and based on the reaction conditions reported in Tables 1 and 2.

All raw materials (monomer and comonomer) and the process solvent (a narrow boiling range high-purity isoparaffinic solvent, Isopar-E) are purified with molecular sieves before introduction into the reaction environment. Hydrogen is supplied pressurized as a high purity grade and is not further purified. The reactor monomer feed stream is pressurized via a mechanical compressor to above reaction pressure. The solvent and comonomer feed is pressurized via a pump to above reaction pressure. The individual catalyst components are manually batch diluted to specified component concentrations with purified solvent and pressured to above reaction pressure. All reaction feed flows are measured with mass flow meters and independently controlled with computer automated valve control systems.

The continuous solution polymerization reactor consists of a liquid full, non-adiabatic, isothermal, circulating, loop reactor which mimics a continuously stirred tank reactor (CSTR) with heat removal. Independent control of all fresh solvent, monomer, comonomer, hydrogen, and catalyst component feeds is possible. The total fresh feed stream to the reactor (solvent, monomer, comonomer, and hydrogen) is temperature controlled by passing the feed stream through a heat exchanger. The total fresh feed to the polymerization reactor is injected into the reactor at two locations with approximately equal reactor volumes between each injection location. The fresh feed is controlled with each injector receiving half of the total fresh feed mass flow. The catalyst components are injected into the polymerization reactor through a specially designed injection stingers. The primary catalyst component feed is computer controlled to maintain the reactor monomer conversion at the specified target. The cocatalyst components are fed based on calculated specified molar ratios to the primary catalyst component Immediately following each reactor feed injection location, the feed streams are mixed with the circulating polymerization reactor contents with static mixing elements. The contents of the reactor are continuously circulated through heat exchangers responsible for removing much of the heat of reaction and with the temperature of the coolant side responsible for maintaining an isothermal reaction environment at the specified temperature. Circulation around the reactor loop is provided by a pump.

The final reactor effluent enters a zone where it is deactivated with the addition of and reaction with a suitable reagent (water). At this same reactor exit location other additives are added for polymer stabilization. For the inventive samples, the conditions were chosen such that at least a 10 fold molar ratio of (hydrate) water vs active catalyst is available to stop the polymerization at the reactor effluent. This aspect is important in order to assure the polymer material has a narrow molecular weight distribution and the composition distribution is maintained narrow.

Following catalyst deactivation and additive addition, the reactor effluent enters a devolatization system where the polymer is removed from the non-polymer stream. The isolated polymer melt is processed and pelletized according to the description provided in WO 2015/191066, pg. 6, 11.23-28, pg. 8, 11. 11-16, and pg. 11, 11.3-25, which is incorporated herein by reference. The non-polymer stream passes through various pieces of equipment which separate most of the ethylene which is removed from the system. Most of the solvent and unreacted comonomer is recycled back to the reactor after passing through a purification system. A small amount of solvent and comonomer is purged from the process.

TABLE 1

| | | Inventive |
|---|---|---|
| Reactor Configuration | Type | Single |
| Comonomer type | Type | 1-octene |
| First Reactor Feed Solvent/Ethylene Mass Flow Ratio | g/g | 3.8 |
| First Reactor Feed Comonomer/Ethylene Mass Flow Ratio | g/g | 0.22 |
| First Reactor Feed Hydrogen/Ethylene Mass Flow Ratio | g/g | 3.6E−04 |
| First Reactor Temperature | °C. | 155 |
| First Reactor Pressure | barg | 34 |
| First Reactor Ethylene Conversion | % | 86.2 |
| First Reactor Catalyst Type | Type | CAT-B |
| First Reactor Co-Catalyst-1 Type | Type | CO-CAT-1 |
| First Reactor Co-Catalyst-2 Type | Type | CO-CAT-2 |
| First Reactor Co-Catalyst-1 to Catalyst Molar Ratio (B to Ti or Zr ratio) | Ratio | 1.2 |
| First Reactor Co-Catalyst-2 Scavenger Molar Ratio (Al to Ti or Zr ratio) | Ratio | 5.0 |
| First Reactor Residence Time | min | 12.9 |

TABLE 2

| Description | Chemical Name |
|---|---|
| CAT-A | dimethyl[[2,2'''-[1,3-propanediylbis(oxy-.kappa.O)]bis[3'',5,5''-tris(1,1-dimethylethyl)-5'-methyl[1,1':3',1''-terphenyl]-2'-olato-.kappa.O]](2-)]-, (OC-6-33)- |
| CAT-B | [N-(1,1-dimethylethyl)-1,1-dimethyl-1-[(1,2,3,4,5-.eta.)-2,3,4,5-tetramethyl-2,4-cyclopentadien-1-yl]silanaminato(2-)-.kappa.N][(1,2,3,4-.eta.)-1,3-pentadiene]-titanium |
| CO-CAT-1 | bis(hydrogenated tallow alkyl)methylammonium tetrakis(pentafluorophenyl)borate(1-) |
| CO-CAT-2 | Aluminoxanes, iso-Bu Me, branched, cyclic and linear; modified methyl aluminoxane |

The reaction resulted in the production of a polymer solution containing a low molecular-weight copolymer having the characteristics as described in the Table 3. "NM" refers to values that were not measured.

TABLE 3

| Characterization Data | | | |
|---|---|---|---|
| | Inventive | Poly. 1 | Poly. 2 |
| Polymer Density (g/cc) | 0.930 | NM | 0.933 |
| Melt Index (I2) or Melt Flow Rate (g/10 min) | NM | NM | 155 |
| Brookfield Viscosity (cP) | 16,850 | NM | 73,570 |
| $M_{n, cc}$ | 8,554 | NM | 6,998 |
| $M_{w, cc}$ | 18,877 | NM | 30,782 |
| $M_{z, cc}$ | 31,142 | NM | 113,479 |
| $M_{w, cc}/M_{n, cc}$ | 2.2 | NM | 4.4 |
| $M_{z, cc}/M_{n, cc}$ | 3.6 | NM | 16.2 |
| w (wt. fraction greater than $10^5$ g/mole) | 0.17% | NM | 4.8% |
| $M_{w, abs}$ | NM | NM | 39,160 |
| $M_{z, abs}$ | NM | NM | 798,722 |
| Tm (°C.) | 113.4 | NM | 125.3 |
| Tc (°C.) | 102.7 | NM | 110.3 |
| ΔTm − Tc | 10.7 | NM | 15.0 |
| CDBI (%) | 79.3 | NM | 35.1 |
| Complex Viscosity at 100 rad/s and 210° C. (Pa·s) | 9.7 | 11.3 | 35.8 |
| Complex Viscosity Ratio (PE/PP) | 0.85 | — | 3.20 |

Nonwoven Process Conditions 5 gsm, 20 gsm, and 40 gsm monolithic meltblown nonwovens are fabricated with a 0.5 meter Hills meltblown line at the European Center for Innovative Textiles (CETI) in Tourcoing, France. A single row core/sheath bicomponent Hills die having a 0.25 mm hole diameter and 35 holes/inch is used for making the nonwoven fabrics. The throughput rate per hole is set at 0.2 g/minute. Air gap is set to be 0.015 inch. Additional processing conditions are shown in Table 4.

TABLE 4

Process Conditions for the Manufacture of Meltblown Nonwovens

| Nonwoven | Material Core | Material Sheath | Melt T Core [°C.] | Melt T Sheath [°C.] | DCD [mm] | Air T at the die [C] | Air speed [m/s] |
|---|---|---|---|---|---|---|---|
| Comparative 1 (monocomponent fiber) | Poly. 1 | Poly. 1 | 240 | | 100 | 260 | 400 |
| Comparative 2 (bicomponent fiber) | Poly. 1 | Poly. 2 | 240 | 230 | 100 | 250 | 330 |
| Comparative 3 (monocomponent fiber) | Inv. | Inv. | 225 | | 100 | 265 | 165 |
| Inventive 1 (bicomponent fiber) | Poly. 1 | Inv. | 240 | 235 | 80 | 250 | 310 |

TABLE 5

Air Permeability of 5 gsm Meltblown Nonwovens

|  | GSM | Air Pearmeability [l/m2/s] |
|---|---|---|
| Comparative 1 | 5.2 | 2789 |
| Comparative 2 | 6.0 | 3605 |
| Comparative 3 | 5.1 | 7274 |
| Inventive 1 | 4.7 | 2547 |

TABLE 6

Air Permeability of 20 gsm Meltblown Nonwovens

|  | GSM | Air Pearmeability [l/m2/s] |
|---|---|---|
| Comparative 1 | 19.9 | 627 |
| Comparative 2 | 20.1 | 719 |
| Comparative 3 | 19.5 | 1505 |
| Inventive 1 | 20.0 | 447 |

TABLE 7

Air Permeability of 40 gsm Meltblown Nonwovens

|  | GSM | Air Pearmeability [l/m2/s] |
|---|---|---|
| Comparative 1 | 39.4 | 212 |
| Comparative 2 | 41.9 | 627 |
| Comparative 3 | 40.8 | 736 |
| Inventive 1 | 40.1 | 200 |

Referring to Tables 5-7, the inventive nonwoven shows improvement in air permeability over comparative nonwovens 1-3 as lower air permeability is an indication of better barrier properties. The inventive nonwoven consistently provides lower air permeability versus comparative nonwovens 1-3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, if any, including any cross-referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A meltblown nonwoven formed from a bicomponent fiber, wherein:
   the bicomponent fiber has a first region and a second region,
   the first region is formed from a first composition comprising at least 75 wt. % of a polypropylene;
   the second region is formed from a second composition comprising at least 75 wt. % of an ethylene/alpha-olefin interpolymer having
   a density of from 0.911 to 0.950 g/cc,
   a Brookfield viscosity at 177° C. from 5,000 cP to 40,000 cP, and
   a molecular weight distribution (Mw,cc/Mn,cc) of 1.8 to 3.5,
   a highest DSC temperature crystallization peak, Tc, from 80° C. to 110° C.;
   the ethylene/α-olefin interpolymer has a temperature differential between a highest DSC temperature melting peak (Tm) and a highest DSC temperature crystallization peak (Tc), (ΔTm-Tc), of less than 16° C.; and
   the bicomponent fiber has a shear viscosity ratio of the first composition to the second composition of less than 2.0.

2. The meltblown nonwoven of claim 1, wherein the ethylene/alpha-olefin interpolymer has an Mz,cc/Mn,cc of less than 3.5.

3. The meltblown nonwoven of claim 1, wherein the ethylene/alpha-olefin interpolymer has a weight fraction (w) of molecular weight greater than $10^5$ g/mole, based on the total weight of interpolymer, as determined by conventional gel permeation chromatography, of less than 2.5%, or alternatively, less than 1.0%.

4. The meltblown nonwoven of claim 1, wherein the ethylene/alpha-olefin interpolymer has a comonomer distribution breadth index of greater than 50%.

5. The meltblown nonwoven of claim 1, wherein the bicomponent fiber has a sheath/core structure.

6. The meltblown nonwoven of claim 5, wherein the first region is a core region and the second region is a sheath region.

7. The meltblown nonwoven of claim 1, wherein the meltblown nonwoven exhibits an air permeability of less than 500 l/m²/s at 20 gsm.

8. A composite structure comprising the meltblown nonwoven of claim 1.

9. The composite structure of claim 8, wherein the composite structure further comprises one or more spunbond nonwovens.

10. A composite structure having a SaMbSc configuration, wherein S is a spunbond nonwoven, M is a meltblown nonwoven of claim 1, and a, b, and c are the number of layers and are independent integers ranging from 1 to 5.

11. The composite structure of claim 10, wherein the spunbond nonwoven is formed from bicomponent fibers having a sheath/core structure, wherein the sheath comprises polyethylene and the core comprises polypropylene.

12. The composite structure of claim 10, wherein the spunbond nonwoven is formed from monocomponent fibers, wherein the monocomponent fibers comprise polyethylene.

13. The meltblown nonwoven of claim 1, wherein the bicomponent fiber has an average diameter less than 10 microns.

* * * * *